(12) United States Patent
Reitmeier

(10) Patent No.: US 9,488,549 B2
(45) Date of Patent: Nov. 8, 2016

(54) SENSOR ELEMENT WITH AIR PRESSURE MEASUREMENT

(71) Applicant: Willibald Reitmeier, Hohenschambach (DE)

(72) Inventor: Willibald Reitmeier, Hohenschambach (DE)

(73) Assignee: Continental Automotive GmbH, Hannover (DE)

( * ) Notice: Subject to any disclaimer, the term of this patent is extended or adjusted under 35 U.S.C. 154(b) by 48 days.

(21) Appl. No.: 14/368,007

(22) PCT Filed: Dec. 20, 2012

(86) PCT No.: PCT/EP2012/076503
§ 371 (c)(1),
(2) Date: Jun. 23, 2014

(87) PCT Pub. No.: WO2013/092925
PCT Pub. Date: Jun. 27, 2013

(65) Prior Publication Data
US 2014/0345361 A1     Nov. 27, 2014

(30) Foreign Application Priority Data

Dec. 23, 2011 (DE) .................. 10 2011 089 888
Jan. 24, 2012 (DE) .................. 10 2012 200 983

(51) Int. Cl.
| | | |
|---|---|---|
| *G01N 27/407* | (2006.01) | |
| *G01M 15/10* | (2006.01) | |
| *G01L 9/00* | (2006.01) | |
| *G01L 19/00* | (2006.01) | |

(52) U.S. Cl.
CPC ......... *G01M 15/104* (2013.01); *G01L 9/0072* (2013.01); *G01L 19/0092* (2013.01); *G01N 27/4071* (2013.01)

(58) Field of Classification Search
CPC ................. G01M 15/104; G01M 15/106
See application file for complete search history.

(56) References Cited

U.S. PATENT DOCUMENTS 4,458,537 A * 7/1984 Bell ................. G01L 13/025
                                                                   73/718
4,869,094 A     9/1989 Kozuka et al.
(Continued)

FOREIGN PATENT DOCUMENTS

| CN | 102084242 | 6/2011 |
|---|---|---|
| DE | 101 17 486 | 10/2002 |

(Continued)

OTHER PUBLICATIONS

Search Report dated Mar. 18, 2013 issued in the corresponding International Patent Application No. PCT/EP2012/076503.
Office Action dated Jul. 11, 2012 issued in the corresponding German Patent Application No. 10 2012 200 983.3.

*Primary Examiner* — Laura Martin
*Assistant Examiner* — Alex Devito
(74) *Attorney, Agent, or Firm* — Cozen O'Connor

(57) ABSTRACT

A sensor element with air pressure measurement includes a layer stack from a plurality of layers arranged one on top of the other. At least one first layer contains a measurement sensor device for measuring a measurement parameter different from an ambient pressure of the sensor. The first or at least one second layer contains a pressure measurement device for measuring the air pressure in an environment on one side of the sensor element, or a channel for coupling a pressure measurement device to an environment on one side of the sensor element.

6 Claims, 8 Drawing Sheets

(56) References Cited

U.S. PATENT DOCUMENTS

| | | | |
|---|---|---|---|
| 5,201,228 A | 4/1993 | Kojima | |
| 6,123,316 A | 9/2000 | Biegelsen et al. | |
| 7,160,750 B2 | 1/2007 | Benzel et al. | |
| 7,354,786 B2 | 4/2008 | Benzel et al. | |
| 7,922,884 B2 | 4/2011 | Strohmaier | |
| 2005/0284137 A1* | 12/2005 | Son | F01N 3/035 60/295 |
| 2007/0144904 A1 | 6/2007 | Strohmaier et al. | |
| 2013/0199829 A1 | 8/2013 | Gottwald | |

FOREIGN PATENT DOCUMENTS

| | | |
|---|---|---|
| DE | 697 24 746 | 3/2004 |
| DE | 10 2004 043 356 | 3/2006 |
| DE | 10 2009 04464 | 5/2011 |
| DE | 10 2010 018 499 | 10/2011 |
| JP | 62 028631 | 2/1987 |
| JP | 64-10144 | 1/1989 |

\* cited by examiner

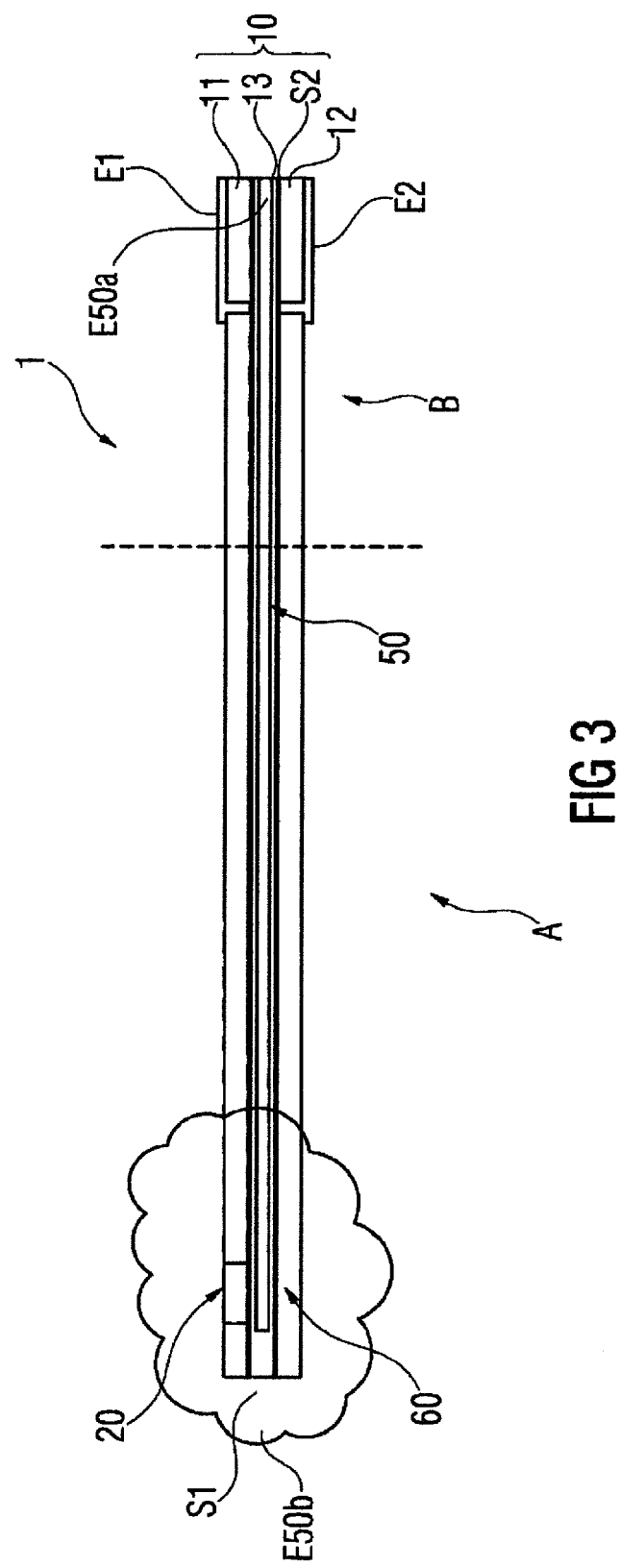

SENSOR ELEMENT WITH AIR PRESSURE MEASUREMENT

CROSS REFERENCE TO RELATED APPLICATIONS

This is a U.S. national stage of application No. PCT/EP2012/076503, filed on Dec. 20, 2012. Priority is claimed on German Application No. DE102011089888.3 filed Dec. 23, 2011, and on German Application No. DE102012200983.3 filed Jan. 24, 2012 the contents of which are incorporated herein by reference.

BACKGROUND OF THE INVENTION

1. Field of the Invention

The invention relates to a sensor element with air pressure measurement, permitting pressure compensation of a measured value determined by the sensor element.

2. Description of Prior Art

Oxygen sensors, particularly in the form of lambda sensors, are used in the automotive field. This type of sensor measures oxygen in a gas volume. However, it is not possible to draw conclusions about the entire oxygen content in the gas volume since the oxygen content that is determined depends on the prevailing partial pressure in the measurement space and, under certain circumstances, also on the reference air if sensors with coupling to a reference air environment are used. In order to determine the air pressure in the environment of the sensor element, air pressure measurement is necessary that is generally carried out with an air pressure sensor separate from the sensor element. After the separate pressure measurement, a computational pressure compensation calculation is subsequently necessary in order to be able to determine the overall oxygen content in the measurement gas.

Document DE 697 24 746 T2 specifies a micro-device carrier system. The micro-device carrier system comprises laminates bonded to one another and that serve as carriers for air ducts, micro-actuators and sensors. The sensors can comprise, inter alia, a pressure sensor that can be embedded in one of the laminate layers.

Document DE 101 17 486 A1 presents various embodiments of a semiconductor component embodied as a thermal conductivity sensor, wherein one embodiment of the thermal conductivity sensor comprises a temperature sensor and a heating element. On the basis of a heating power necessary to maintain a defined or constant temperature, an ambient pressure and/or a type of gas or composition of a gas can be determined.

Document DE 10 2010 018 499 A1 relates to a printed circuit board multi-layer structure having a layer stack and a cavity in the interior of the layer stack. The cavity is subjected to an ambient pressure through an opening provided in the layer stack and is covered by a liquid-impermeable diaphragm. According to one embodiment, the diaphragm can permit gas diffusion.

Document DE 10 2009 044 645 A1 relates to a method for producing at least one cavity in a microelectronic and/or micromechanical structure using at least one sacrificial layer, wherein by sublimating the material of the sacrificial layer the sacrificial layer is removed and a cavity is formed in the structure.

Document DE 10 2004 043 356 A1 relates to a method for producing a micromechanical sensor element in which a cavity is formed in a substrate by a trench etching process composed of two trenching steps of different chronological length. The sensor element can be used, inter alia, to detect a pressure variable and an air mass.

SUMMARY OF THE INVENTION

It is desirable to specify a sensor element with air pressure measurement, which makes it possible for the pressure measurement which is necessary for the pressure compensation of the measured value determined by the sensor element to be carried out directly with the sensor element.

According to one embodiment, a sensor element with air pressure measurement comprises a layer stack composed of a plurality of layers which are arranged one on top of the other, wherein at least one first layer contains a measurement sensor device for measuring a measurement variable which is different from an ambient pressure of the sensor. At least one second layer contains a pressure measurement device for measuring the air pressure in an environment on one side of the sensor element or a duct for coupling a pressure measurement device to an environment on one side of the sensor element.

In the sensor element, the pressure measuring function is added to the measurement sensor device contained in the layer stack and has the purpose of measuring a measurement variable different from an ambient pressure of the sensor. The measurement sensor device can be designed, for example, for measuring the oxygen content of the environment of the sensor element. The pressure measuring device can be of a design suitable for carrying out absolute and relative pressure measurements. The duct for coupling the pressure measurement device can be contained in a layer of the layer stack for conducting gas to an external pressure measurement device. When the sensor element has a permanently heated measuring tip, the latter serves at the same time as a cleaning barrier with respect to moisture and particles (pyrolysis) for the start of the air duct in the substrate. The pressure measurement device can be arranged in such a way that the air pressure measurement takes place in an exhaust gas environment as well as in the cool, clean contact region of a reference environment. Parts of the electrodes used for measuring oxygen can be used to make contact with the pressure measurement device.

The sensor element can be structured in accordance with the standard multilayer ceramic technology. The pressure measurement cell can be adjusted by grinding the wafer surfaces of the layer stack. In order to narrow the tolerances, the region of the layer stack in which a cavity region of the pressure measurement device is arranged can be ground and polished.

Further embodiments of the sensor element can be found in the dependent claims.

BRIEF DESCRIPTION OF THE DRAWINGS

The invention will be explained in more detail below with reference to figures which show exemplary embodiments of the present invention. In the drawings:

FIG. 3 shows an embodiment of a sensor element in a planar design;

DETAILED DESCRIPTION OF THE PRESENTLY PREFERRED EMBODIMENTS

Figure 1:
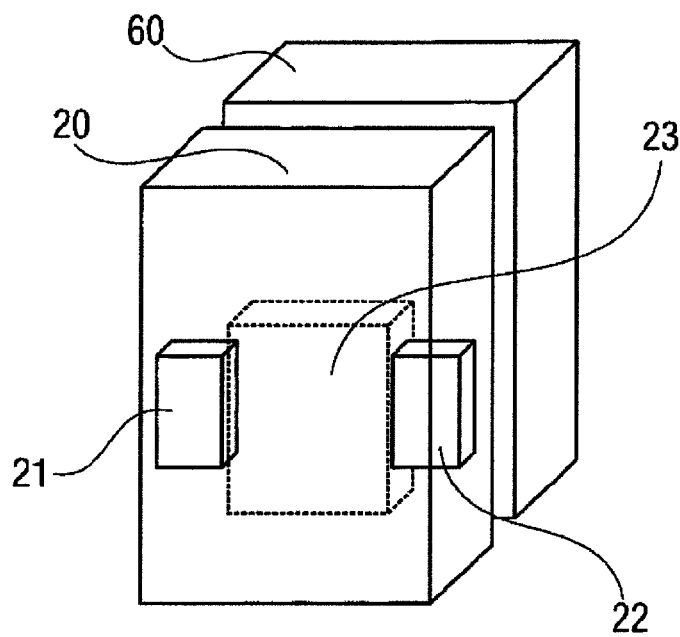
FIG. 1 shows an embodiment of a broadband probe for determining an oxygen content of a gas.

FIG. 1 shows an embodiment of a sensor element for measuring an oxygen content in an environment of the sensor element which is embodied as a broadband probe. The broadband probe comprises a measurement sensor device 20 and a heating device 60. The measurement sensor device 20 has porous diffusion passages 21, 22 and a detection chamber 23. The diffusion passages and the detection chamber can be arranged in a substrate made of zirconium oxide ($ZrO_2$). The heating device 60 can be embodied as a ceramic heating element contained in a substrate made of aluminum oxide ($Al_2O_3$).

Figure 2A:
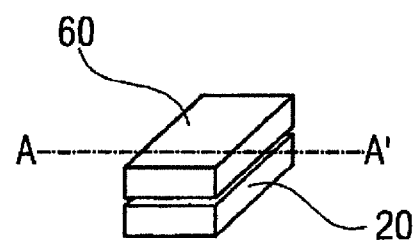
FIG. 2A shows a perspective view of a planar element and a heating device of a broadband probe.
Figure 2B:
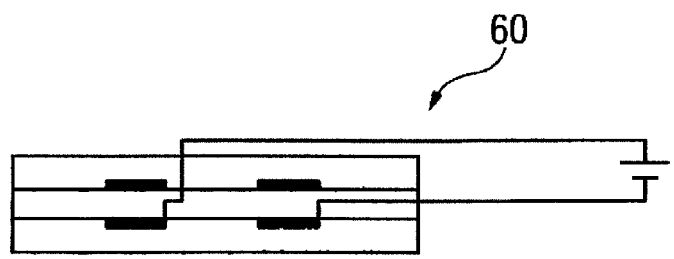
FIG. 2B shows a cross section through a heating device of a broadband probe.
Figure 2C:
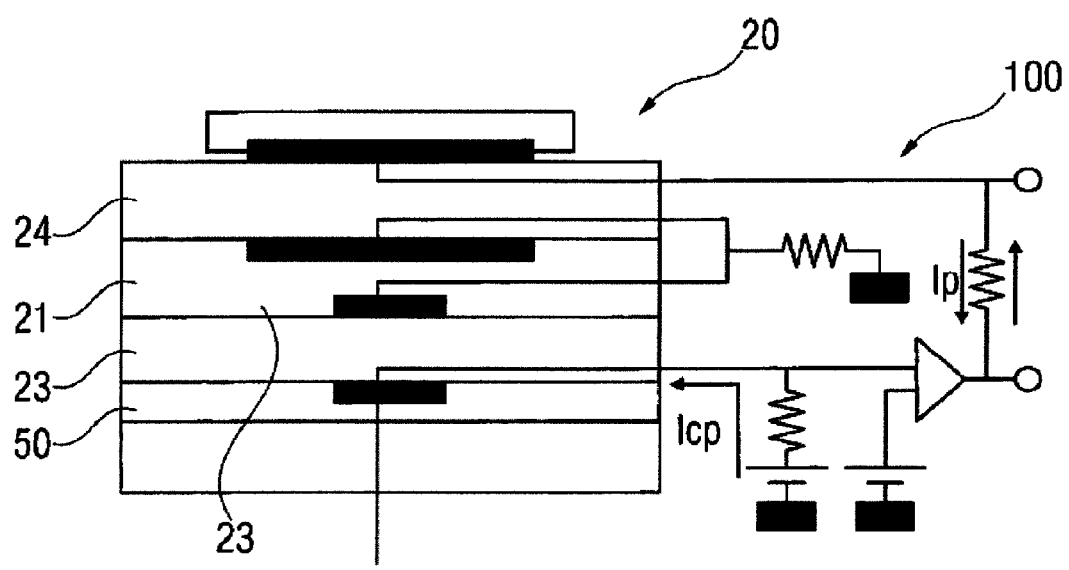
FIG. 2C shows a cross section through a planar element of a broadband probe.

FIG. 2A shows a perspective view of the sensor element with the measurement sensor device 20 for measuring an oxygen content and the heating device 60, which are arranged one on top of the other in a stack arrangement. FIG. 2B shows a cross-sectional view in the region A-A' of the sensor element through the heating device 60, and FIG. 2C shows a cross-sectional view in the region A-A' of the sensor element through the measurement sensor device 20. The measurement sensor device 20 is of a suitable design for measuring an oxygen content in the environment of the sensor element and comprises a sensor cell 23 and a pump cell 24 arranged one on top of the other in a layer stack. An evaluation circuit 100 produces a pump current 1p between electrode terminals A1 and A2, which pump current 1p is the measurement variable for the lambda value in the environment of the oxygen measurement sensor device.

In order to measure the oxygen content of the environment of the sensor element, the gas from the environment passes into the measurement chamber 23 via the porous diffusion passages 21, 22, in which measurement chamber 23 the oxygen content is detected using measurement electrodes and compared with a setpoint value. As a result of this comparison measurement, the pump current 1p is then activated, the pump current 1p adjusting the oxygen concentration in the detection chamber 22 to a setpoint value. By a sensor pump current 1cp, the lambda value which is measured in this way can be passed on to a control device for evaluation. The pump current is proportional to the residual oxygen content in the environment of the sensor element.

Figure 4:
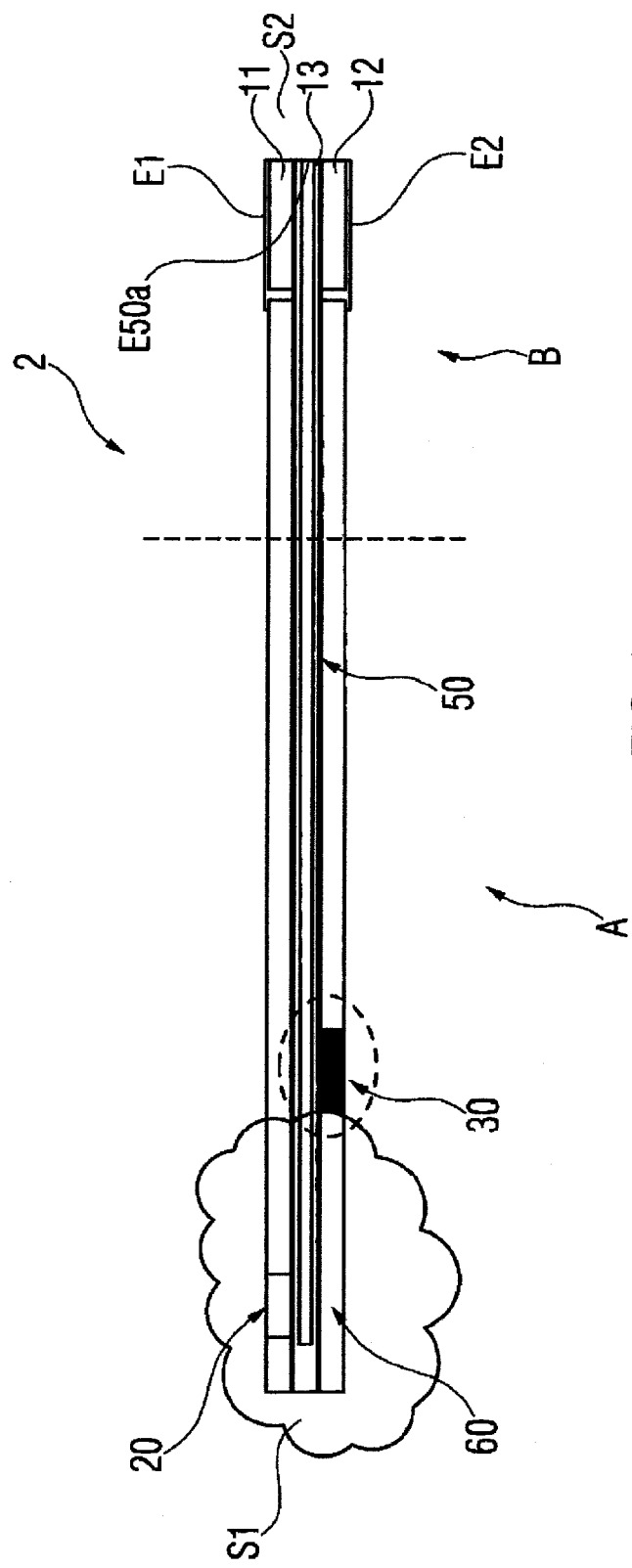
FIG. 4 shows an embodiment of a sensor element with air pressure measurement.
Figure 7:
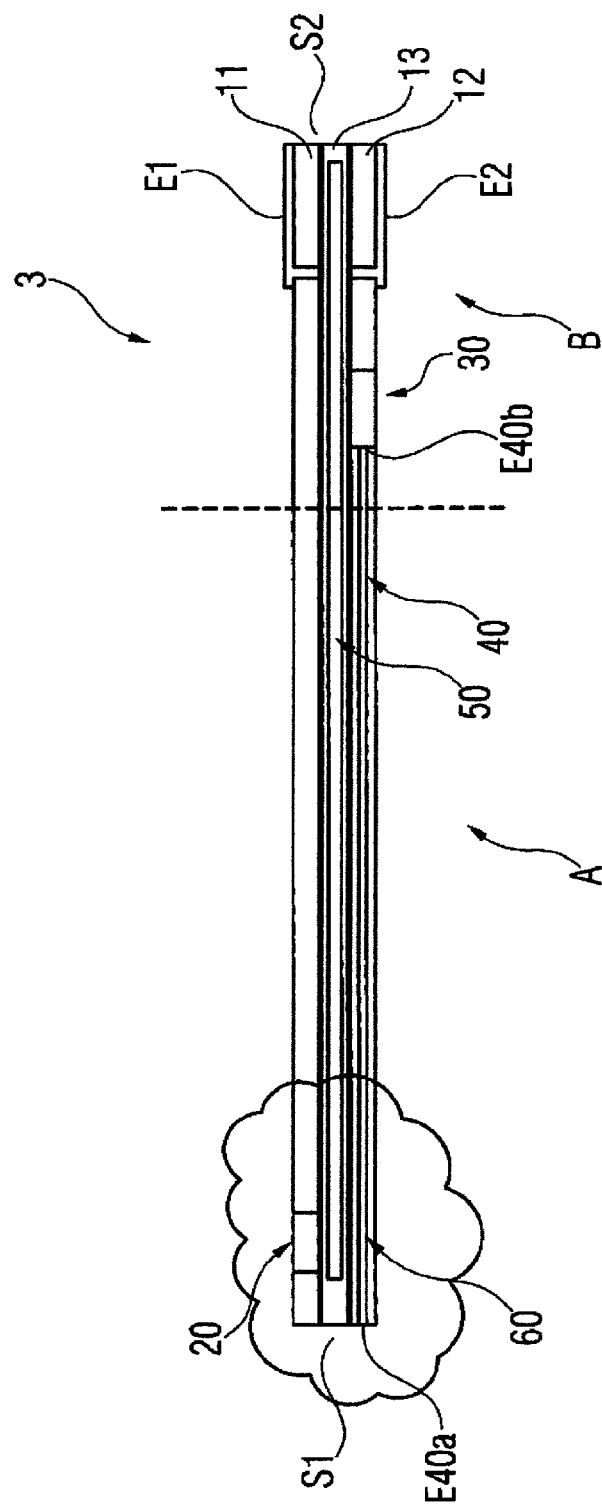
FIG. 7 shows a further embodiment of a sensor element with air pressure measurement.

FIGS. 3, 4, 7 and S each show an embodiment of a sensor element in a planar design, which sensor element is suitable for measuring an oxygen content in an environment of the sensor element. The sensor element can be designed, in particular, as a lambda sensor. The sensor element has a layer stack 10 composed of a plurality of layers 11, 12 and 13 which are arranged one on top of the other. The layer stack 10 can be constructed from ceramic materials. The layer 11 is designed to be conductive to oxygen ions at a high temperature of, for example, more than 650° C. and can for this purpose contain, for example, zirconium oxide. The measurement sensor device 20, which, according to the design shown in FIG. 2C, can have the sensor cell, the measurement chamber and the pump cell, is arranged in the layer 11 on one side S1 of the sensor element 1.

The layer 12 can be embodied as an isolation layer and can have a material made of aluminum oxide ($Al_2O_3$). The layer 12 can contain the heating device 60 near to the side S1 of the sensor element under the measurement sensor device 20. The heating device 60 is designed to heat a diffusion region around the measurement sensor device 20. A duct 50 is arranged in the layer 13 arranged between the layers 11 and 12. The layer 13 can also be an insulation layer which contains a material made of aluminum oxide. One end E50a of the duct 50 opens into an environment of the sensor element. Another end E50b of the duct 50 ends in the layer 13 between the measurement sensor device 20 and the heating device 60. The duct 50 ends in a section of the layer 13 under the measurement sensor device 20 and above the heating device 60. The duct 50 is embodied as a reference air duct through which the oxygen-containing reference air from the environment of the sensor element passes to the diffusion region with the measurement sensor device 20. In order to make contact with the measurement sensor device 20, electrode terminals E1 are provided on the layer 11. Electrode terminals E2 on the layer 12 serve to make electrical contact with the heating element 60.

The sensor element can be used to determine an oxygen content in a measurement gas in the environment of the sensor element. For this purpose, a section A of the sensor element is introduced into the measurement environment. The measurement environment can be, for example, an exhaust gas stream. A section B of the sensor element is arranged in the environment of the reference air.

An oxygen value in the measuring environment around the measurement sensor device 20 can be determined with the sensor element 1 in FIG. 3. The oxygen value that is determined is dependent on the partial pressure in the gas volume of the measuring environment. In order to infer the real oxygen content in the measurement gas in the environment of the measurement sensor device, the partial pressures of the measurement gas on the side S1 of the sensor element must also be measured on the left of the dot-dashed line, and those of the reference air in the reference environment on the side S2 of the sensor element to the right of the dot-dashed line. The dot-dashed line graphically separates the measurement environment from the environment of the reference air.

In a first approximation, the partial pressure of the reference air is assumed to be constant if ambient pressure is assumed. In the embodiments 2 and 3 of a sensor element shown in FIGS. 4 and 7 for measuring an oxygen content of the environment of the sensor element, at least one of the layers of the layer stack 10 contains a pressure measurement device 30. In the embodiment 4 of the sensor element shown in FIG. 8, one of the layers of the layer stack contains a duct for coupling a pressure measurement device 30 to an environment of the sensor element. The pressure measurement device 30 is designed to measure the air pressure in the environment of the sensor element.

In the embodiment 2 (illustrated in FIG. 4) of the sensor element, the layer 12 contains the pressure measurement device 30 for measuring the ambient pressure of the sensor element. The pressure measurement device 30 is arranged here closer to the measurement sensor device 20 than to the end E50a of the reference air duct 50. Furthermore, the pressure measurement device 30 is arranged closer to the heating device 60 than to the end E50a of the reference air duct. The pressure measurement device 30 can therefore also be located in the heated region of the sensor element.

Figure 5A:
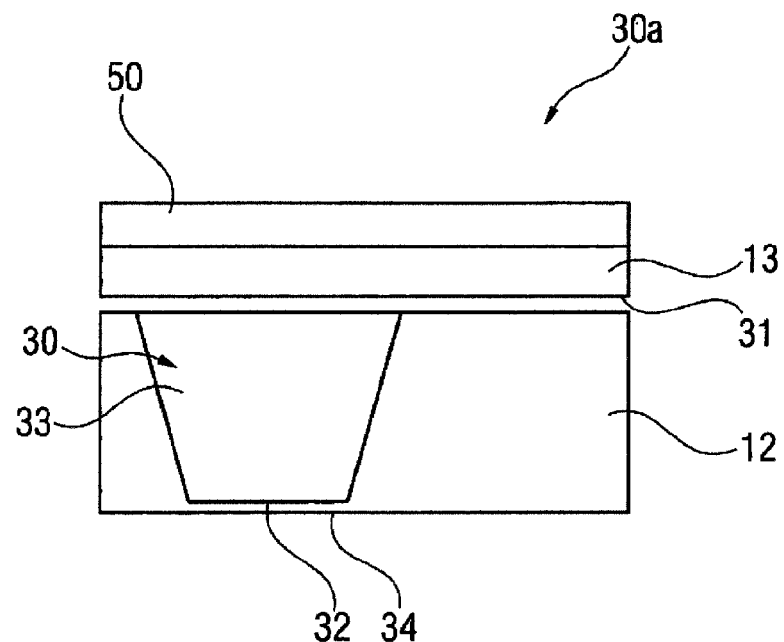
FIG. 5A shows an embodiment of a pressure measurement device of a sensor element with air pressure measurement.
Figure 5B:
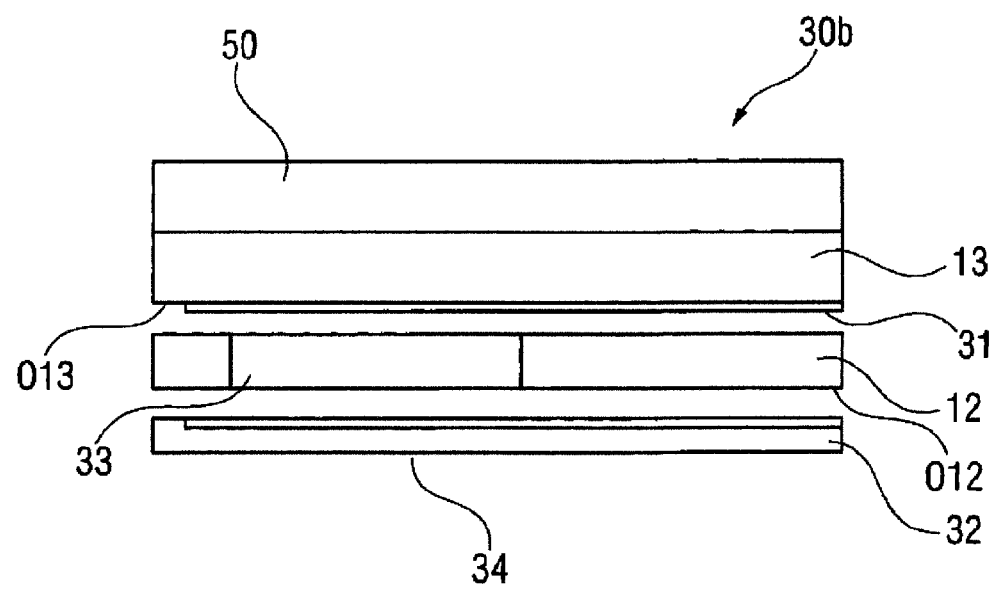
FIG. 5B shows an embodiment of a pressure measurement device of a sensor element with air pressure measurement.
Figure 6A:
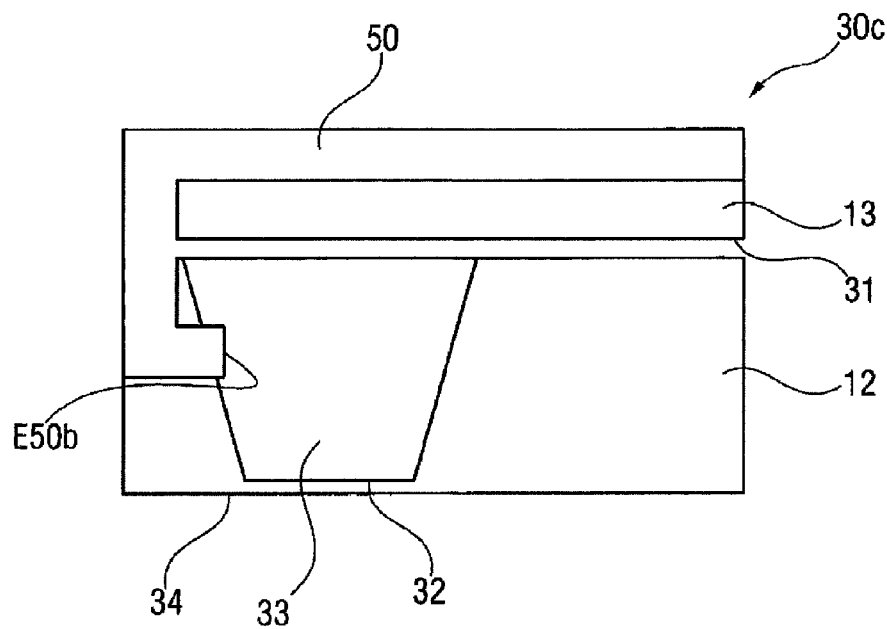
FIG. 6A shows an embodiment of a pressure measurement device of a sensor element with air pressure measurement.
Figure 6B:
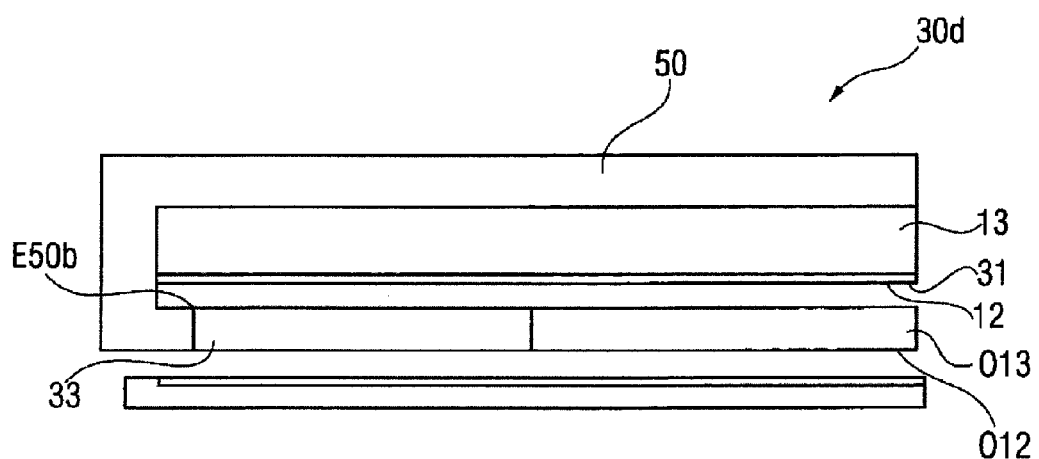
FIG. 6B shows an embodiment of a pressure measurement device of a sensor element with air pressure measurement.

FIGS. 5A, 5B, 6A and 6B show embodiments of the pressure measurement device 30. The pressure measurement device 30 is embodied as a capacitive pressure sensor with an electrode 31, an electrode 32, a cavity 33 and a diaphragm 34. The electrodes 31 and 32 are arranged on opposite sides of the cavity 33. The cavity 33 is formed in the layer 12. The electrode 31 is arranged on a surface O13 of the layer 13 under the duct 50. In the embodiments of the pressure measurement device shown in FIGS. 5A and 6A, the electrode 32 is arranged on the bottom and optionally on the side walls of the cavity 33. As is shown in FIGS. 5B and 6B, the electrode 32 can be arranged on a surface O12 of the layer 12 facing away from the layer 13. The electrode 31 is arranged on the surface O13 of the layer 13 facing the layer 12.

In the embodiments shown in FIGS. 5A and 5B, the pressure measurement device 30 is embodied as an absolute pressure measurement device. In contrast to this, in the embodiments shown in FIGS. 6A and 6B, the pressure measurement device is embodied as a relative pressure measurement device. The reference air duct 50 for feeding in the reference air opens into the cavity 33 at an end E50b of the duct in the embodiments shown in FIGS. 6A and 6B. As is illustrated by way of example in FIG. 6A, the duct 50 can be arranged in the layer 13 and can lead from there into the cavity 33 or as a further embodiment, illustrated by dot-dashed lines in FIG. 6A the duct 50 can run in the layer 12 and lead from there into the cavity 33.

FIG. 7 shows an embodiment 3 of the sensor element in which the pressure measurement device 30 is arranged in the layer 12 closer to the end E50a of the reference air duct 50 than to the heating device 60 or the measurement sensor device 20. A duct 40 is provided for coupling the pressure measurement device 30 to the measurement environment on the side S1 of the sensor element 3, in the insulation layer 12. The duct 40 opens, at one end E40a on the side S1 where the sensor element is, into the environment of the sensor element in which the measurement gas is contained. Another end E40b of the reference duct 40 for the pressure measurement ends in the layer 12 and opens into the cavity 33 of the pressure measurement device 30. The end E40a can be embodied as a free opening or as an open-pore, gas-permeable layer, for example composed of a ceramic.

In the embodiments 2 and 3 of the sensor element, the pressure measurement cavity 33 of the pressure measurement device 30 is implemented in the multilayer structure 10. In the embodiment 4 of the sensor element shown in FIG. 8, the layer stack 10 contains only the duct 40 for coupling the pressure measurement device 30 to the environment of the sensor element. The layer 12 can contain the pressure duct 40. The pressure duct 40 opens with one end E40a on the side S1 of the sensor element into the measurement environment, and at one end E40b on the side S2 of the sensor element on which the electrode terminals E1, E2 are arranged on different sides of the layer stack 10, into an environment of the reference air of the sensor element. The pressure measurement device 30 is connected at the end E40b to the pressure duct 40 or a further pressure transmission piece, for example a hose, is intermediately connected between the end E40b and the pressure measurement device 30.

Figure 8:
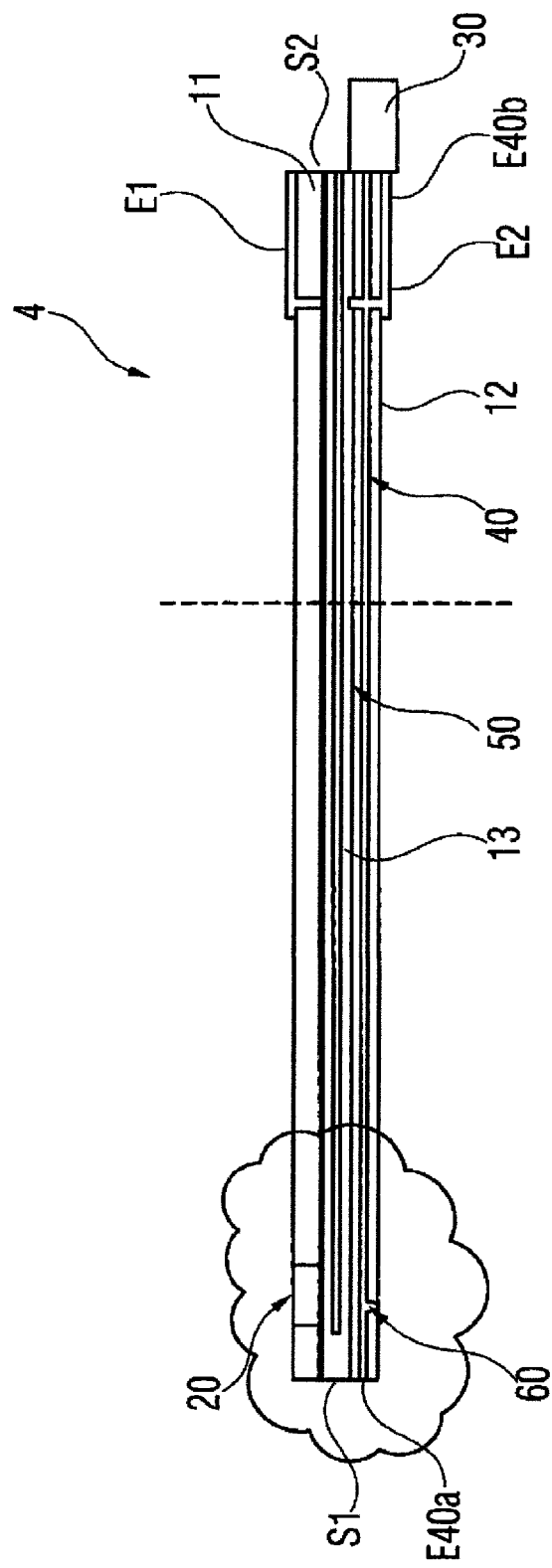
FIG. 8 shows a further embodiment of a sensor element with air pressure measurement.

In the embodiments of the sensor element illustrated in FIGS. 7 and 8, the multilayer conducts the pressure of the measurement medium. In the embodiment of the sensor element 3 which is shown in FIG. 7, in which embodiment the pressure measurement device 30 and the pressure duct 40 are arranged in the layer stack, the pressure measurement can be carried out in the clean, cold contact region away from the heating device 60 and the measurement environment. At the end E40a of the pressure duct 40, the air enters the duct 40 after being cleaned. The continuously heated measuring tip of the sensor element serves as a cleaning barrier with respect to moisture and particles (pyrolysis) for the start of the air duct in the substrate. Since the pressure measurement device 30 is arranged close to the electrode terminals E1, E2, short signal paths to a connected evaluation electronics are produced.

In the embodiment of the sensor element shown, basically one combination of the sensor principles is always possible. If the measurement sensor device is designed, for example, for measuring particles, for example the interdigital electrode structure can be used as an electrode of the pressure measurement device for measuring the particles. The structure shown can also be used for sensor elements with measurement sensor devices which are intended for other uses, for example for detecting gases or for determining moisture.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A sensor element with air pressure measurement, comprising:
 a layer stack (10) having a plurality of layers (11, 12, 13) arranged one on top of the other,
 wherein a first layer (11) of the layer stack (10) has a measurement sensor device (20) configured to measure a measurement variable different from an ambient pressure of the sensor,
 wherein the first layer (11) of the layer stack (10), or a second layer (12) of the layer stack (10), has a pressure measurement device (30) arranged spatially separately from the measurement sensor device (20) and configured to measure air pressure in an environment on one side (S1) of the sensor element or a duct (40) configured to couple a pressure measurement device (30), arranged externally with respect to the layer stack (10), to an environment on the one side (S1) of the sensor element, wherein the sensor element has a heating device (60) configured to heat a region of the sensor element around the measurement sensor device (20), and the measurement sensor device (20) and the heating device (60) are arranged one on top of the other in the layer stack (10), wherein the first layer (11), the second layer (12) or a third layer (13) of the layer stack contains a further duct (50), one end (E50a) of the further duct (50) opening into surroundings of the sensor element on another side (S2) of the sensor element, and wherein the pressure measurement device (30) is arranged closer to the one end (E50a) of the further duct (50) than to the heating device (60).

2. A sensor element with air pressure measurement, comprising:

a layer stack (10) having a plurality of layers (11, 12, 13) arranged one on top of the other, wherein a first layer (11) of the layer stack (10) has a measurement sensor device (20) configured to measure a measurement variable different from an ambient pressure of the sensor, wherein the first layer (11) of the layer stack (10), or a second layer (12) of the layer stack (10), has a pressure measurement device (30) arranged spatially separately from the measurement sensor device (20) and configured to measure air pressure in an environment on one side (S1) of the sensor element or a duct (40) configured to couple a pressure measurement device (30), arranged externally with respect to the layer stack (10), to an environment on the one side (S1) of the sensor element, wherein the sensor element has a heating device (60) configured to heat a region of the sensor element around the measurement sensor device (20), and the measurement sensor device (20) and the heating device (60) are arranged one on top of the other in the layer stack (10), wherein one end (E40a) of the duct (40) opens into the surroundings of the sensor element on the one side (S1), and another end (E40b) of the duct (40) is coupled to the pressure measurement device (30), and wherein the other end (E40b) of the duct (40) ends in the second layer (12) of the layer stack.

3. A sensor element with air pressure measurement, comprising:

a layer stack (10) having a plurality of layers (11, 12, 13) arranged one on top of the other, wherein a first layer (11) of the layer stack (10) has a measurement sensor device (20) configured to measure a measurement variable different from an ambient pressure of the sensor, wherein the first layer (11) of the layer stack (10), or a second layer (12) of the layer stack (10), has a pressure measurement device (30) arranged spatially separately from the measurement sensor device (20) and configured to measure air pressure in an environment on one side (S1) of the sensor element or a duct (40) configured to couple a pressure measurement device (30), arranged externally with respect to the layer stack (10), to an environment on the one side (S1) of the sensor element, wherein the sensor element has a heating device (60) configured to heat a region of the sensor element around the measurement sensor device (20), and the measurement sensor device (20) and the heating device (60) are arranged one on top of the other in the layer stack (10), wherein the first layer (11), the second layer (12) or a third layer (13) of the layer stack contains a further duct (50), one end (E50a) of the further duct (50) opening into surroundings of the sensor element on another side (S2) of the sensor element, wherein the pressure measurement device (30) comprises a capacitive pressure sensor with a first electrode (31), a second electrode (32), a cavity (33) and a diaphragm (34), wherein the first and second electrodes (31, 32) are arranged on opposite sides of the cavity (33), and wherein the diaphragm (34) is arranged in one of the layers (12) of the layer stack in which the cavity (33) is arranged, on the side of the second electrode (32) facing away from the cavity (33).

4. The sensor element as claimed in claim 3, wherein another end (E50b) of the further duct (50) opens into the cavity (33).

5. The sensor element as claimed in claim 3, wherein the layer stack (10) has the third layer (13) between the first and second layers (11, 12), wherein the first electrode (31) is arranged on a surface (013) of the third layer (13) facing the second layer (12), and wherein the second electrode (32) is arranged on a surface (O12) of the second layer (12) facing away from the third layer (13).

6. The sensor element as claimed in claim 5, wherein the measurement sensor device (20) has electrode terminals (E1) for applying or tapping a voltage, and wherein the first and second electrodes (31, 32) of the pressure measurement device (30) are each connected to one of the electrode terminals (E1) of the measurement sensor device (20).

\* \* \* \* \*